US007230039B2

(12) United States Patent
Trieu et al.

(10) Patent No.: US 7,230,039 B2
(45) Date of Patent: Jun. 12, 2007

(54) BIOACTIVE NANOCOMPOSITES AND METHODS FOR THEIR USE

(75) Inventors: Hai H. Trieu, Cordova, TN (US); Kimberly A. Chaffin, Plymouth, MN (US)

(73) Assignee: SDGI Holdings, Inc., Wilmington, DE (US)

( * ) Notice: Subject to any disclaimer, the term of this patent is extended or adjusted under 35 U.S.C. 154(b) by 80 days.

(21) Appl. No.: 10/630,092

(22) Filed: Jul. 30, 2003

(65) Prior Publication Data

US 2004/0024081 A1 Feb. 5, 2004

(51) Int. Cl.
*A61F 2/00* (2006.01)
(52) U.S. Cl. .................... 523/113; 523/114; 523/115
(58) Field of Classification Search ................ 523/113, 523/114, 115
See application file for complete search history.

(56) References Cited

U.S. PATENT DOCUMENTS

| | | | |
|---|---|---|---|
| 4,131,597 A | 12/1978 | Bluethgen et al. | |
| 4,192,021 A | 3/1980 | Deibig et al. | |
| 4,437,836 A | 3/1984 | Schmitz-Josten et al. | |
| 4,516,276 A | 5/1985 | Mittelmeier et al. | |
| 4,623,553 A | 11/1986 | Ries et al. | |
| 4,636,526 A | 1/1987 | Dorman et al. | |
| 4,743,229 A | 5/1988 | Chu | |
| 4,776,890 A | 10/1988 | Chu | |
| 4,888,366 A | 12/1989 | Chu et al. | |
| 5,001,169 A | 3/1991 | Nathan et al. | |
| 5,002,582 A | 3/1991 | Guire et al. | |
| 5,015,247 A | 5/1991 | Michelson | |
| 5,035,715 A | 7/1991 | Smestad et al. | |
| 5,091,344 A | 2/1992 | Enomoto et al. | |
| 5,123,925 A | 6/1992 | Smestad et al. | |
| 5,204,319 A | 4/1993 | Enomoto et al. | |
| 5,217,492 A | 6/1993 | Guire et al. | |
| 5,246,457 A | 9/1993 | Piez et al. | |
| 5,273,964 A | 12/1993 | Lemons | |
| 5,320,844 A | 6/1994 | Liu | |
| 5,338,772 A | 8/1994 | Bauer et al. | |
| 5,364,399 A | 11/1994 | Lowery et al. | |
| 5,380,298 A | 1/1995 | Zabetakis | |
| 5,468,544 A | 11/1995 | Marcolongo et al. | |
| 5,480,438 A | 1/1996 | Arima et al. | |
| 5,645,934 A | 7/1997 | Marcolongo et al. | |
| 5,669,909 A | 9/1997 | Zdeblick et al. | |
| 5,679,723 A | 10/1997 | Cooper et al. | |
| 5,721,049 A | 2/1998 | Marcolongo et al. | |
| 5,728,753 A | 3/1998 | Bonfield et al. | |
| 5,776,193 A | 7/1998 | Kwan et al. | |
| 5,782,919 A | 7/1998 | Zdeblick et al. | |
| 5,817,328 A | 10/1998 | Gresser et al. | |
| 5,858,318 A | 1/1999 | Luo | |
| 5,914,356 A | 6/1999 | Erbe | |
| 5,964,807 A | 10/1999 | Gan et al. | |
| 5,972,368 A | 10/1999 | McKay | |
| 5,977,204 A | 11/1999 | Boyan et al. | |
| 6,027,742 A | 2/2000 | Lee et al. | |
| 6,033,438 A | 3/2000 | Bianchi et al. | |
| 6,139,585 A | 10/2000 | Li | |
| 6,152,927 A | 11/2000 | Farris et al. | |
| 6,165,486 A | 12/2000 | Marra et al. | |
| 6,270,347 B1 * | 8/2001 | Webster et al. ............. | 433/173 |

FOREIGN PATENT DOCUMENTS

| | | |
|---|---|---|
| EP | 0 747 067 A2 | 12/1996 |
| WO | WO 00/57932 | 10/2000 |
| WO | WO 01/01930 | 1/2001 |
| WO | WO 01/54746 | 8/2001 |
| WO | WO 02/22117 | 3/2002 |

OTHER PUBLICATIONS

Allograft Catalog, University of Florida Tissue Bank, Inc., LIT.UF. CT96 Rev. A/98.
Tangent Cortical Wedge Mechanical Testing, Regeneration Technologies, Inc., ©1999 RTI.
Flahiff, C.M. et al., "Analysis of a biodegradable composite for bone healing", *Journal of Biomedical Materials Research*, 32:419-424 (1996).
Verheyen, C.C.P.M. et al., "Hydroxylapatite/poly(L-lactide) composites: An animal study on push-out strengths and interface histology", *Journal of Biomedical Materials Research*, 27:433-444 (1993).
Verheyen, C.C.P.M. et al., "Evaluation of hydroxylapatite/poly(L-lactide) composites: Mechanical behavior", *Journal of Biomedical Materials Research*, 26:1277-1296 (1992).
Furukawa, T. et al., "Histomorphometric study on high-strength hydroxyapatite/poly(L-lactide) composite rods for internal fixation of bone fractures", *Journal of Biomedical Materials Research*, 50:410-419 (2000).
Yasunaga, T. et al., "Bonding behavior of ultrahigh strength unsintered hydroxyapatite particles/poly(L-lactide) composites to surface of tibial cortex in rabbits", *Journal of Biomedical Materials Research*, 47:412-419 (2000).
Watanabe, S. et al., "Traumatic Sternal Segment Dislocation in a Child", *CHEST*, 96(3):684-686 (1989).
Shikinami, Y. et al., "Bioresorbable devices made of forged composites of hydroxyapatite (HA) particles and poly-L-lactide (PLLA): Part I. Basic characteristics", *Biomaterials*, 20:859-877 (1999).

(Continued)

*Primary Examiner*—Edward J. Cain
(74) *Attorney, Agent, or Firm*—Woodard, Emhardt, Moriarty, McNett & Henry LLP (57) ABSTRACT

Orthopedic compositions are provided that include a homogeneous mixture of a biocompatible polymer and a bioactive particulate ceramic wherein the ceramic has an average particle size of not more than 500 nm are provided. The compositions may be used to form bone cement or various spinal implants, including spinal spacers, interbody fusion cages, bone plates and bone screws. Methods for stabilizing a spine, for correcting a bone defect, and for promoting fusion of adjacent vertebrae are also provided.

20 Claims, 5 Drawing Sheets

OTHER PUBLICATIONS

Doyle, C. et al., *"In vitro* and *in vivo* evaluation of polyhydroxybutyrate and of polyhydroxybutyrate reinforced with hydroxyapatite", *Biomaterials*, 12:841-847 (1991).

Higashi, S. et al., "Polymer-hydroxyapatite composites for biodegradable bone fillers", *Biomaterials*, 7:183-187 (1986).

Bonfield, W. et al., "Hydroxyapatite reinforced polyethylene—a mechanically compatible implant material for bone replacement", *Biomaterials*, 2:185-186 (1981).

Hamadouche, M. et al., "The *In vivo* Bioactivity of Sol-Gel Bioactive Glasses Coated Alumina Implants", 46th Annual Meeting, Orthopaedic Research Society, 0174 (2000).

Orefice, R.L. et al., "Processing and Characterization of Bioactive Polysulfone-Bioglass® Composites", *Bioceramics*, 8:409-414, Eds. Wilson, J. et al., Florida, USA, Perganon (1995).

Liu, Qing et al.: "Nano-apatite/polymer composites: mechanical and physicochemical characteristics". BIOMATERIALS, 1997 Elsevier Science Limited, GB. ISSN: 0142-9612.

* cited by examiner

BIOACTIVE NANOCOMPOSITES AND METHODS FOR THEIR USE

BACKGROUND OF THE INVENTION

The present invention relates to composite materials that may be shaped to form a wide variety of prostheses for orthopedic applications. Specifically, compositions that are composites of a biocompatible polymer and a particulate ceramic are provided, wherein the particulate ceramic has an average particle size of not more than about 500 nm.

The intervertebral disc functions to stabilize the spine and to distribute forces between vertebral bodies. A normal disc includes a gelatinous nucleus pulposus, an annulus fibrosis and two vertebral end plates. The nucleus pulposus is surrounded and confined by the annulus fibrosis.

Intervertebral discs may be displaced or damaged due to trauma or disease. Disruption of the annulus fibrosis allows the nucleus pulposus to protrude into the spinal canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process. As a disc dehydrates and hardens, the disc space height will be reduced, leading to instability of the spine, decreased mobility and pain.

One way to relieve the symptoms of these conditions is by surgical removal of a portion or all of the intervertebral disc. The removal of the damaged or unhealthy disc may allow the disc space to collapse, which could lead to instability of the spine, abnormal joint mechanics, nerve damage, as well as severe pain. Therefore, after removal of the disc, adjacent vertebrae are typically fused to preserve the disc space.

Several devices exist to fill an intervertebral space following removal of all or part of the intervertebral disc in order to prevent disc space collapse and to promote fusion of adjacent vertebrae surrounding the disc space. Many of the implants, including intervertebral disc spacers, as well as cervical plates along with bone screws utilized to hold the plates in place, have been made of metal. Due to the stiffness of the material, some metal implants, such as intervertebral disc spacers, may stress shield the bone, thereby increasing the time required for fusion. Subsidence, or sinking of the device into bone, may also occur when metal implants are implanted between vertebrae if fusion is delayed.

In order to solve the problems associated with metal implants, a wide variety of bone grafts and substitutes thereof have been used. Autograft is often preferred because it is osteoinductive, although allograft may also be used. However, such sources of grafts provide several disadvantages. Autograft is available in only limited supply. Moreover, the additional surgery increases the risk of infection and blood loss and may reduce structural integrity at the donor site. Additionally, some patients complain that the graft harvesting surgery causes more short-term and long-term pain than the fusion surgery.

Allograft material, which is obtained from donors of the same species, is more readily obtained. However, allogeneic bone does not have the osteoinductive potential of autogenous bone and may thus provide only temporary support. The slow rate of fusion using allografted bone can lead to collapse of the disc space before fusion is accomplished.

Several attempts have been made to develop a material that may be used to form an implant, such as an intervertebral disc implant or other load bearing structure, which avoids the disadvantages of metal implants and bone implants. Calcium phosphate-based implants are known, but are brittle in many cases and may thus not have sufficient load bearing capacity for a desired application. Synthetic polymers are also known, but have several drawbacks, including their small load bearing capacity and their minimal or non-existent bone bonding capacity. Although compositions of synthetic polymers and hydroxapatite, typically sized in the micrometer range, have been made in order to combine the advantages of the polymers and the calcium phosphate-based ceramics, and have obtained a certain degree of success, a need for improved compositions for orthopedic use still exists. The present invention addresses this need.

SUMMARY OF THE INVENTION

Orthopedic compositions that are composites of a homogeneous mixture of a biocompatible polymer and a bioactive particulate ceramic wherein the ceramic has an average particle size of not more than about 500 nm are provided. The increased surface area of the particles and their interaction with the various polymers provide the compositions with advantageous biological and mechanical properties. In preferred forms of the invention, the composition is comprised predominantly of a polymer such that the polymer forms a matrix into which the ceramic particles are embedded. In further preferred forms of the invention, a composition is provided that includes a bioactive particulate ceramic embedded in a biocompatible polymer matrix wherein the ceramic has an average particle size of not more than about 500 nm.

The compositions may be used to form, for example, shaped articles and bone cements for orthopedic applications. For example, the compositions may be used to form various spinal implants, including various spinal spacers and cages, as well as bone plates and bone screws. Methods for stabilizing a spine that include associating with vertebrae of a spine a shaped, load bearing article formed from the compositions described herein are also provided. Further provided are methods of correcting bone defects which include applying to the defect the compositions described herein. Moreover, methods of promoting fusion of adjacent vertebrae are described that include providing an implant formed from the compositions described herein, preparing adjacent vertebrae to receive the implant in an intervertebral disc space between adjacent vertebrae and positioning the implant in the disc space after the preparation step.

It is an object of the invention to provide compositions that are composites of a biocompatible polymer and a particulate ceramic wherein the composite has advantageous mechanical and biological properties.

It is further object of the invention to provide methods for stabilizing a spine, methods for correcting bone defects and methods for promoting fusion of adjacent vertebrae that utilize the compositions described herein.

These and other objects and advantages of the present invention will be apparent from the descriptions herein.

DESCRIPTION OF THE PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would norm ally occur to one skilled in the art to which the invention relates.

The present invention relates to bioactive nanocomposites and methods for their use in orthopedics. In certain forms of the invention, the nanocomposites include a homogeneous mixture of a biocompatible polymer and a bioactive particulate ceramic wherein the ceramic has an average particle size of not more than about 500 nm. In further preferred forms of the invention, the ceramic particles are embedded or otherwise dispersed in a polymer matrix. The increased surface area of the ceramic phase may advantageously enhance the interactions between the two phases for improved mechanical and biological properties as more fully described below. The nanocomposites may advantageously be used to form a shaped article useful as a bone-bone fixation device, bone-soft tissue fixation device, a tissue replacement or other similar graft or device. For example, the nanocomposites may form shaped articles such as load bearing intervertebral cages, bone screws, such as interference screws, bone plates such as, for example, cervical plates, and various joint replacements or artificial discs. Moreover, the nanocomposites may further form a bone cement for advantageous use in arthoplasty, cranioplasty, vertebroplasty and other similar applications. Methods for stabilizing a spine and for correcting bone defects utilizing the compositions of the present invention are also provided.

In one aspect of the invention, a composition is provided that is a composite including a homogeneous mixture of a bioactive particulate ceramic and a biocompatible polymer. The components are sufficiently mixed together such that they are intermingled to form the composition. The average particle size of the bioactive particulate ceramic is advantageously not more than about 500 nm, such as about 1 nm to about 500 nm. Other preferred sizes include an average particle size of not more than about 250 nm, preferably an average size of not more than about 100 nm and most preferably an average particle size of not more than about 50 nm. Typical average particles sizes include about 1 nm to about 250 nm, about 1 nm to about 100 nm and about 1 nm to about 50 nm.

In further forms of the invention, at least about 30%, preferably at least about 50% and further preferably at least about 75% of the particulate ceramic has an average particle size of not more than about 400 nm, preferably not more than about 300 nm, further preferably not more than about 200 nm, more preferably not more than about 100 nm and most preferably not more than about 50 nm to about 100 nm.

The ceramic phase is a bioactive material in that it may elicit a biological response at its surface which results in bond formation with adjacent tissue. The ceramic phase can be chosen from a wide variety of ceramics, including synthetic, natural, bioresorbable or non-resorbable ceramics. For example, the ceramic phase may include bioactive glass and various calcium-containing ceramics, such as calcium phosphate-containing ceramics and including hydroxyapatite, α-tricalcium phosphate, β-tricalcium phosphate, and tetracalcium phosphate. The calcium-containing ceramics may include other various salts of calcium, such as calcium sulfate, calcium carbonate as well as a combination of these and/or the above-referenced ceramics. The calcium-containing ceramics may be sintered or unsintered as known in the art.

A feature of the invention includes use of particulate ceramic having a large surface area. For example, the surface area of the particulate ceramic is at least about 10 $m^2/g$, further preferably at least about 20 $m^2/g$, but typically at least about 40 $m^2/g$. The ceramic maintains its particulate nature in the composite. Additionally, the calcium:phosphate ratio in the calcium phosphate-containing ceramic may vary, but may be about 1.50 to about 2.00, preferably about 1.50 to about 1.70, and more preferably about 1.60 to about 1.67. Moreover, the particulate ceramic may further be porous, with a porosity of about 1% to about 80%, further preferably about 1% to about 50%. The porosity may be adjusted as desired to, for example, control the rate of delivery of various pharmacological agents as further described below.

The particulate ceramics may be isolated or synthesized by methods known in the art, such as described in U.S. Pat. Nos. 6,013,591; 5,858,318 and 5,676,976, or may be purchased commercially. For example, the nanocrystalline apatite particles may be formed by precipitating apatite from a solvent by adding calcium salt to a phosphate source with a pH of about 7 to about 14 followed by aging at a temperature of about −25° C. and above 100° C., and, if necessary, by wet grinding.

In certain forms of the invention as mentioned above, a combination of hydroxyapatite and another calcium-containing material, such as another calcium phosphate-containing material, act as the particulate ceramic component. In such an embodiment, it is preferred that the ratio of hydroxyapatite to other calcium-containing material is about 1:2 to about 20:1.

The biocompatible polymer, such as a reinforcing polymer, may similarly be obtained from natural or synthetic sources, and may also be bioresorbable or non-bioresorbable. The biocompatible polymer may be selected such that it will act to reinforce the composite in order to, for example, increase the load bearing capability of the composite. Examples of natural materials the polymer may be composed of include collagen, elastin, silk, and demineralized bone matrix. Examples of non-resorbable synthetic materials include polyethylene, polymethylmethacrylate, polyetheretherketone, and polyurethane. Suitable bioresorbable synthetic polymers include poly(L-lactide), poly(D,L-lactide), poly(L-co-D,L-lactide), polyglycolide, poly(lactide-co-glycolide), poly(hydroxylbutyrate), poly(hydroxyvalerate), tyrosine-derived polycarbonate, polyanhydride, polyorthoester, polyphosphazene, poly(dioxanone), poly(ε-caprolactone), and polyglyconate. Other similar polymers known to the art may be used and various combinations of polymers may be included in the composition to adjust the properties of the composition as desired.

The molecular weight of the polymers may vary depending on the desired application, but is preferably not more than about $1 \times 10^6$ Daltons. Further preferred molecular weights of the polymers include about 50,000 to about 750,000, about 100,000 to about 500,000 and about 200,000 to about 400,000 Daltons.

The polymers may be provided in a variety of forms, depending on the desired application. Suitable forms include gels, powders, pellets, granules, and liquids. The polymers may be polymerized from monomers as known in the art or may be purchased commercially.

Each component of the composition is present in an amount sufficient to impart or otherwise increase a beneficial property on the composition. For example, the polymer may be present in an amount sufficient to decrease the brittleness of the particulate ceramic or otherwise increase the flexibility of, or reinforce the ceramic. As a further example, the particulate ceramic may be present in an amount sufficient to increase the rigidity of the polymer. Each component may ultimately be present in an amount sufficient to increase the load bearing capacity, ductility and/or flexibility of the composition.

As an example, the particulate ceramic may be present in the composition in an amount of about 1% to about 49% by volume of the composition and in other forms of the invention about 1% to about 25% by volume of the composition, the remainder being made up of the polymer. The composition may further include about 10% to about 40%, and further about 20% to about 30% by volume of the ceramic, the remainder made up of the polymer. Thus, the polymer may be present in the composition in an amount of about 51% to about 99%, about 75% to about 99%, about 60% to about 90%, and about 70% to about 80%, all on a volume basis. In preferred forms of the invention, the composition is predominantly composed of a polymer matrix, and the particulate ceramic is embedded in the matrix. In other forms, the composition is composed predominantly of a particulate ceramic into which is embedded, or which is otherwise combined with, the desired polymer or combination of polymers.

The compositions may be prepared by mixing the polymer and ceramic together and may be processed using conventional processing methods for thermoplastics and thermoset polymers as known in the art, including injection molding, compression molding, extrusion, transfer molding, solution casting or in-situ polymerization. Homogeneous mixing of the two phases, so that the two components will be sufficiently intermingled, may be achieved by a variety of methods, including polymer mixing methods known to the art, including, for example, blending, extrusion, and solvent suspension. Carrier solvents may be utilized as a carrier for, for example, the polymer, ceramic, or both, or particle surface treatments may be applied to facilitate homogeneous mixing. For example, tetrahydrofuran, ethanol or water may be utilized, or the surface of the particle may be treated with heat, plasma or surfactants. Post-processing treatments such as pressure/thermal treatments, annealing, forging and machining, as done in the manufacture of polymers and ceramics may be performed on the compositions if desired. The processing treatments are selected to insure that particle nature of the ceramic is maintained so that, in certain forms of the invention, a majority of, and preferably substantially all of, the ceramic particles are preferably individually surrounded by the polymer.

As one example, in order to achieve homogeneous mixing of a polymer and a calcium phosphate-containing-ceramic, such as hydroxyapatite, the polymer can first be dissolved in a miscible solvent. Hydroxyapatite can then be added to the polymer solvent mixture, wherein the hydroxyapatite carrier solvent is immiscible with the polymer solvent. The hydroxyapatite will settle to the heavier polymer rich solvent phase, creating a solvent/polymer/hydroxyapatite blend. The hydroxyapatite carrier solvent can be eliminated, leaving the miscible solvent, polymer and hydroxyapatite. The low viscosity of the solvated system aids the uniform dispersion of the hydroxyapatite within the polymer. The blend (polymer/hydroxyapatite/solvent) can be quenched into a solution in dry ice and methanol. The polymer and the hydroxyapatite will separate from the solvent and can be recovered. One advantage of the quenching step is that, especially when a polymer matrix is utilized, the finest possible dispersion of hydroxyapatite within the polymer matrix is maintained.

As a further example of achieving homogeneous mixing of a polymer and hydroxyapatite, dry blending of the polymer and hydroxyapatite can be accomplished after recovering the hydroxyapatite from its carrier solvent through vacuum filtration and drying. In this case, plasma treatment of the hydroxyapatite surface may be required to prevent aggregates of hydroxyapatite from forming. Such methods are well-known, and are similar to plasma treatment methods developed in the silicone industry.

The composition may advantageously deliver desired pharmacological agents, especially when one or both components of the implant are resorbable. The pharmacological agent may include a growth factor that may increase the rate of fusion, or may have some other beneficial effect. A wide variety of growth factors may advantageously be employed in the present invention. For example, the growth factor may include a bone morphogenetic protein, LIM mineralization proteins (LMPs), transforming growth factors, such as transforming growth factor-$\beta$(TGF-$\beta$), insulin-like growth factors, platelet-derived growth factors, fibroblast growth factors, or other similar growth factor that has some beneficial effect.

The growth factors, or other pharmacological agents, are typically included in the composition in therapeutically effective amounts. For example, the growth factors may be included in the compositions in amounts effective in promoting fusion. Although these amounts will depend on the specific case, the compositions may typically include no more than about five weight percent of the growth factors, and preferably no more than about one weight percent of the growth factors.

In a preferred form of the invention, the growth factor is a bone morphogenetic protein. Recombinant human bone morphogenetic proteins (rhBMPs) are further preferred because they are available in large quantities and do not transmit infectious diseases. Most preferably, the bone morphogenetic protein is a rhBMP-2, rhBMP-4 or heterodimers thereof. However, any bone morphogenetic protein is contemplated, including bone morphogenetic proteins designated as BMP-1 through BMP-18.

BMPs are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All bone morphogenic proteins are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In other forms of the invention, the pharmacological agent may be one that is used for treating various spinal conditions, including infected spinal cords, cancerous spinal cords and osteoporosis. Such agents include antibiotics, analgesics and anti-inflammatory drugs, including steroids. Other such agents are well know to the skilled artisan. These agents are also used in therapeutically effective amounts that will treat the various conditions and the symptoms they cause. Such amounts may be determined by the skilled artisan depending on the specific case.

The pharmacological agents are preferably dispersed within the composition for in vivo release. The porosity of the composition may be adjusted in order to achieve the appropriate level of porosity to release the pharmacological agents at a desired rate. The pharmacological agents may be added to the composition prior to it being formed into a shaped article, if desired, by adding the agents to the composition, as long as the processing conditions will not adversely affect the agent. Alternatively, the compositions may form a shaped or other article as more fully described below and these articles may be soaked in an appropriate solution containing the agent, or by other appropriate methods known to the skilled artisan.

Figure 1:
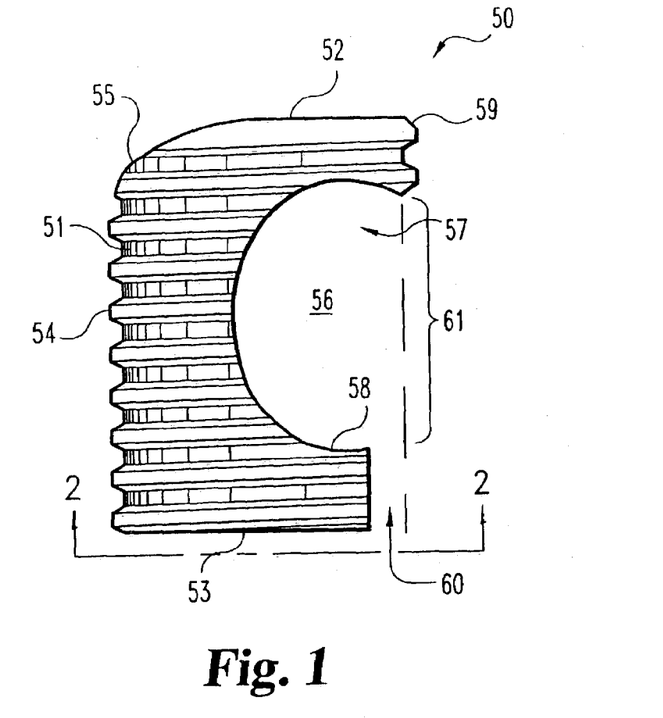
FIG. 1 is a perspective view of an intervertebral disc implant that may be formed from the compositions of the present invention.
Figure 2:
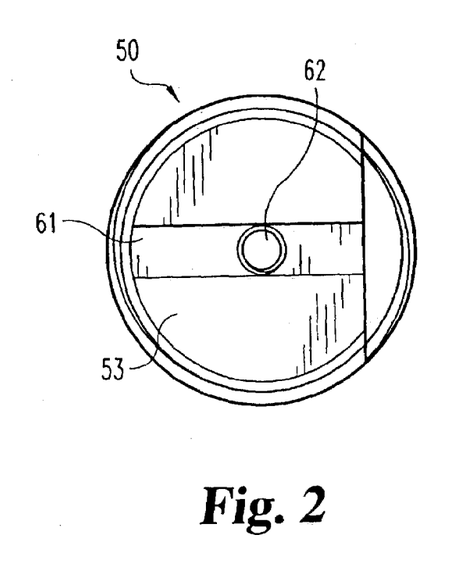
FIG. 2 is a side view of the implant of FIG. 1.

The compositions of the present invention have a wide variety of applications. For example, the compositions may form composites that may be load bearing and may form a shaped article, such as an intervertebral disc implant, including a fusion cage. Referring now to FIGS. 1 and 2, various intervertebral disc implants are shown. Implant 50 is an open chambered C-shaped spacer having a body 51 with a tool engagement end 53 and an opposite insertion end 52. Body 51 includes threads 54 and a wall 55 wherein the wall defines a chamber 56 between the two ends 52 and 53 and including an opening 57 in communication with chamber 56. In one form of the invention a seen in FIG. 1, first arm 58 is truncated relative to second arm 59, forming a channel 60 in communication with mouth 61 and chamber 56. The tool engagement end includes an adjustment score mark or groove 61 and a tool engaging or instrument attachment hole 62. In other forms of the invention, both first arm 58 and second arm 59 are the same length. Such implants, as well as other implants that may be formed utilizing the advantageous compositions described herein, are shown and described further in U.S. Pat. No. 6,033,438 to Bianchi et al.

Figure 3:
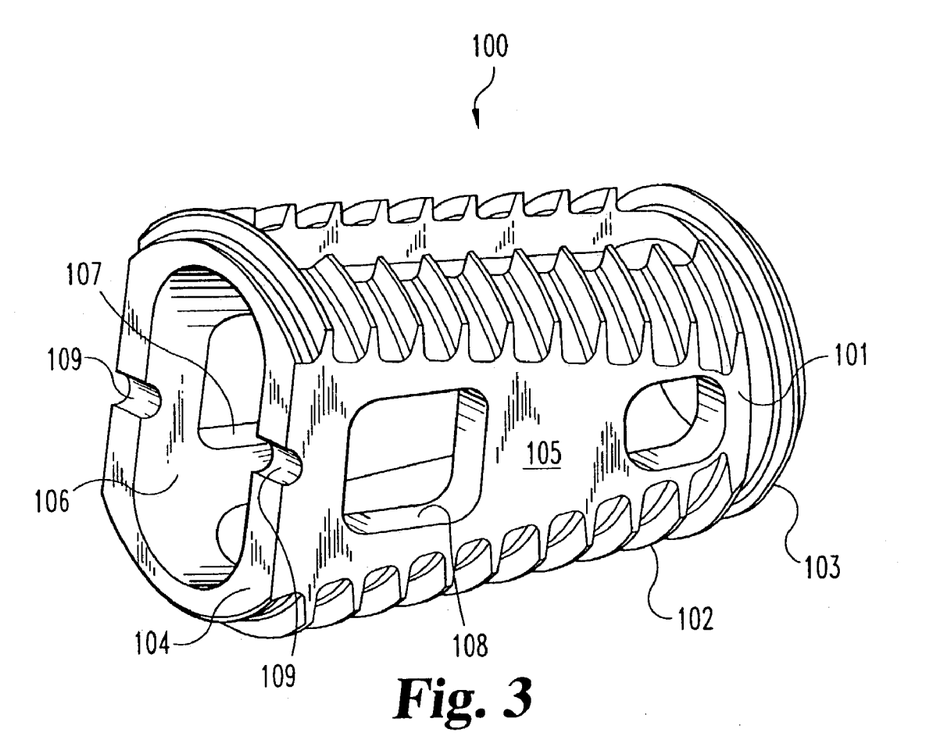
FIG. 3 is a side perspective view of another intervertebral disc implant, such as an interbody fusion device, that may be formed from the compositions described herein.

Referring now to FIG. 3, an interbody fusion device 100, or cage, is shown. The device is a conical body 101 that defines a series of interrupted external threads 102 and a complete thread 103 at the leading end of the implant. Conical body 101, and particularly body wall 104, includes parallel truncated side walls 105. The device preferably has a hollow interior 106, as well as vascularization openings 107 and 108 defined through each of the truncated side walls 105. Diametrically opposed notches 109 may be provided which are configured to engage an implant driver tool. Openings 107 and 108 are sized to provide optimum passage for vascularization. Such a device, and various forms of the device, is shown and described in U.S. Pat. Nos. 5,669,909 and 5,782,919. A wide variety of other spinal implants may be formed from the compositions described herein, including those described in U.S. Pat. No. 5,015,247 to Michelson.

Figure 4:
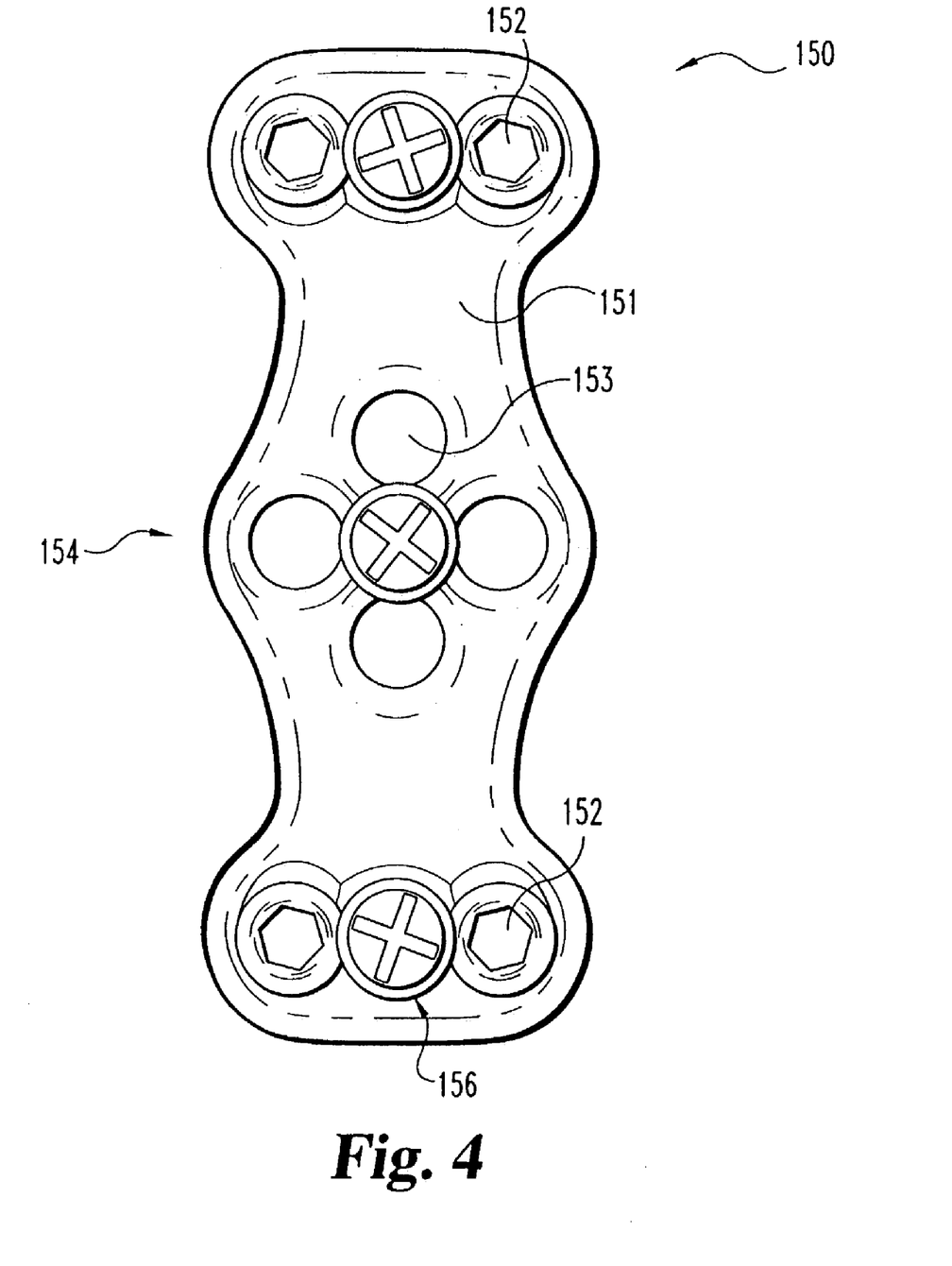
FIG. 4 is an end view of a cervical plate that may be formed from the compositions of the present invention.
Figure 5:
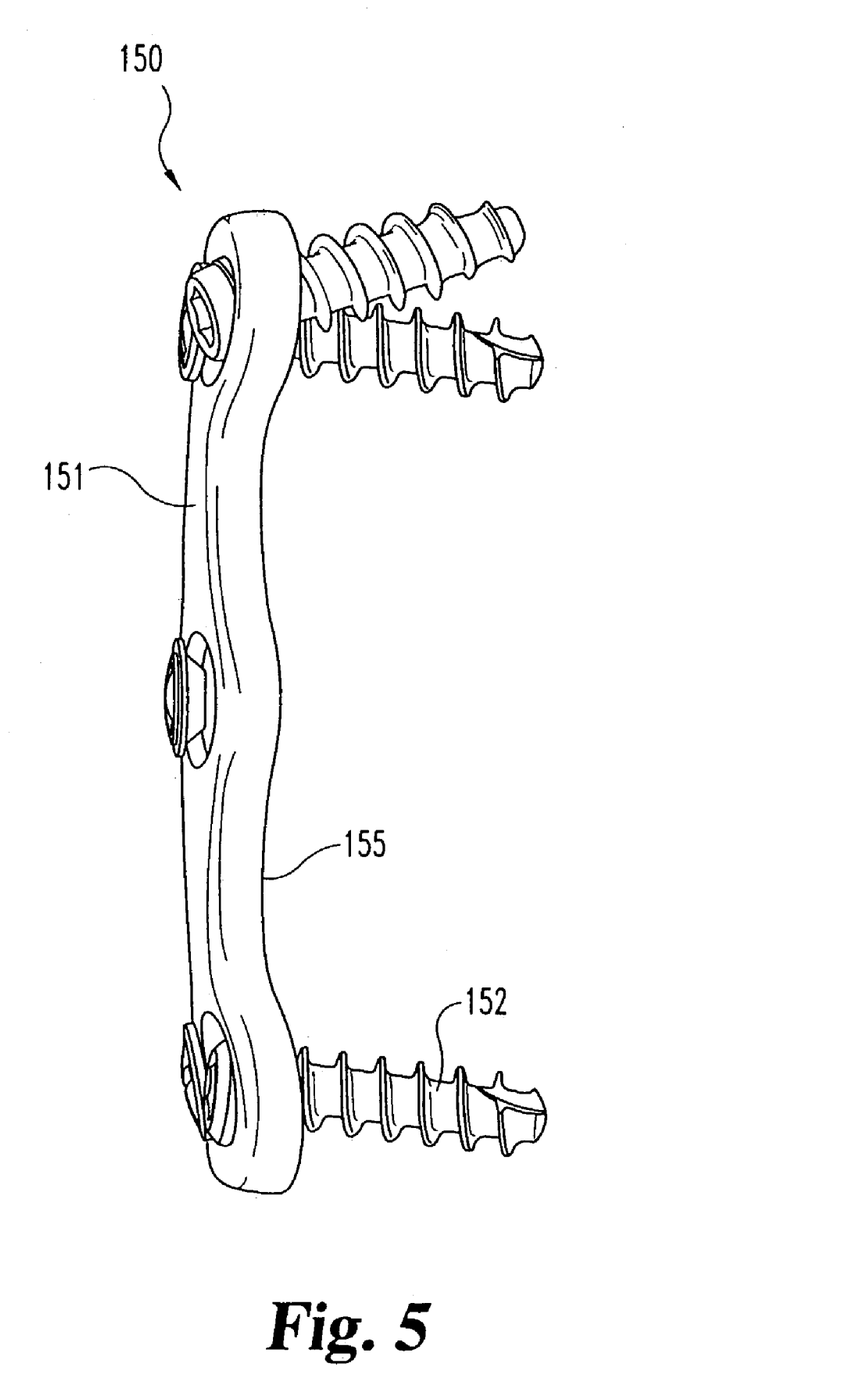
FIG. 5 is a side view of the cervical plate of FIG. 4.

Referring now to FIGS. 4–7, various bone plates are shown. The implant shown in FIGS. 4 and 5 is an anterior plating system or fixation assembly 150. System 150 includes an elongated plate 151 and a number of bone screws 152. Elongated plate 151 is provided with a plurality of screw holes 153 that may be present in a variety of arrangements, such as the four-hole pattern 154 as seen in FIG. 4. Bottom surface 155 of plate 151 is preferably configured to contact and engage the vertebral bodies at each of the instrumented levels of the spine. Bone screws 152 are held to plate 151 by way of a plurality of locking assemblies 156. Such plates are described, for example, in U.S. Pat. No. 6,152,927 to Farris et al.

Figure 6:
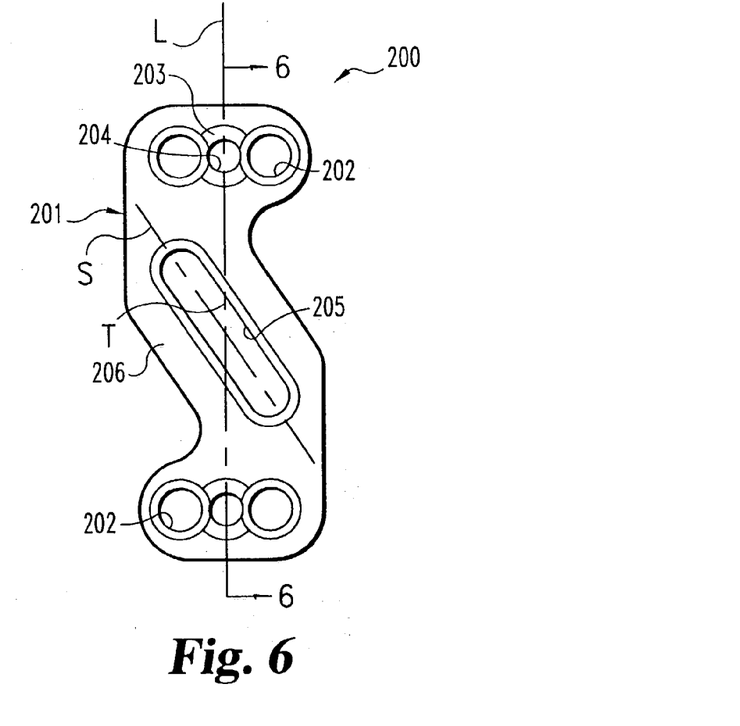
FIG. 6 is an end view of a cervical plate that may be formed from the compositions of the present invention.
Figure 7:
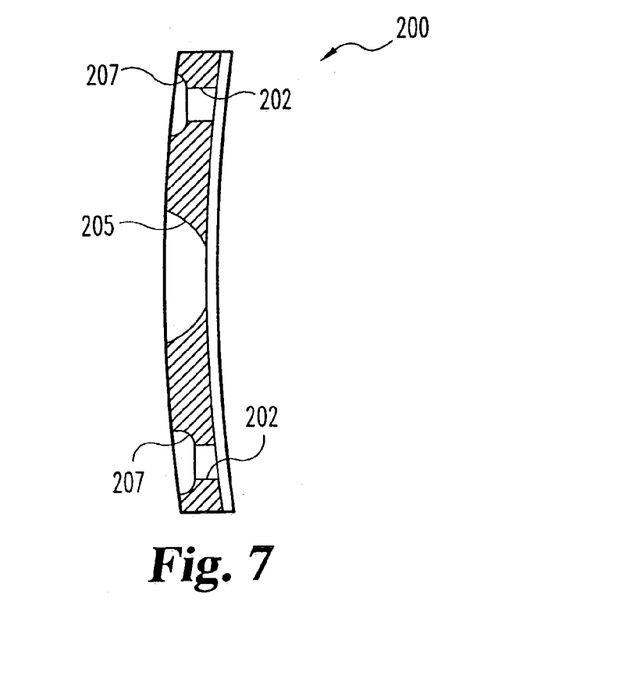
FIG. 7 is a side view of the cervical plate of FIG. 6.

Referring now to FIGS. 6 and 7, yet another example of a bone plate is seen. The implant is a cervical plate 200 that includes an elongated fixation plate 201. Plate 201 includes a plurality of screw bores 202 defined in the plate as well as screw bore recesses 207. A screw fixation means 203, such as threaded fixation bore 204, serves to prevent the screws from working loose over time. Plate 201 further defines a slot 205 formed within bridge portion 206 of the plate, wherein slot 205, or the axis S along the length of the slot, is oriented at an acute angle T to the longitudinal axis L of plate 201. Such plates are described, for example, in U.S. Pat. No. 5,364,399 to Lowery et al. A wide variety of other bone plates and screws known in the art may be formed from the compositions described herein.

The compositions described herein provide a number of other advantages not discussed up to this point. For example, when a polymer is combined with a particulate ceramic, such as hydroxyapatite in combination with other forms of calcium phosphate, the ceramic may advantageously promote bone apposition. Moreover, although such cages may be strong due to the biphasic reinforcement structure, the cages may gradually lose their strength upon in vivo degradation and eventual resorption. As a further advantage of such cages formed of hydroxyapatite and/or other forms of calcium phosphate in combination with a resorbable polymer, the nano-particles of the ceramic may buffer the acidic degradation products of the resorbable polymer. Additionally, such cages can be located in vivo radiographically due to the presence of hydroxyapatite and/or other calcium phosphates. Moreover, the ceramic may advantageously act as a support structure to enhance bone ingrowth in the compositions described herein and, in other forms of the invention, may act to reinforce the polymer it is combined with. For example, the nanometer-sized ceramic particles may be more beneficial in promoting bone ingrowth than larger particles, including those greater than about 1 micron.

In yet other forms of the invention, the compositions may be processed to form a bone cement. The bone cement is flowable or otherwise moldable at a temperature below the body temperature of a mammal, such as about 30° C., and especially at ambient or room temperature (about 17° C. to about 25° C.), and is preferably hardened in-situ at about body temperature (37° C.) or ambient temperature as described herein. In such forms of the invention, it is preferred that the polymer utilized is in a liquid, gel or paste form, although other forms may be suitable, as long as the bone cement is in a pliable or otherwise moldable form for application.

In yet other aspects of the invention, methods of stabilizing a spine are provided. In one form, a method includes associating with vertebrae of the spine a shaped, load bearing article formed from the compositions described herein. For example, a bone plate may be associated with, or otherwise attached to, adjacent vertebrae, by methods known to the skilled artisan. Such stabilization may prove useful, for example, in various spinal fusion procedures.

In other aspects of the invention, methods of promoting fusion of adjacent vertebrae are provided. In one form, a method includes providing an implant, preferably a load bearing implant as described herein, formed from the compositions described herein and preparing adjacent vertebrae to receive the implant in an intervertebral disc space between adjacent vertebrae. Such preparation methods are well known to the skilled artisan, and may include removing all or a portion of the intervertebral disc, including all or a portion of the nucleus pulposus. The implant may then be positioned in the intervertebral disc space between the adjacent vertebrae after the preparation step.

In further aspects of the invention, methods for correcting a bone defect are provided. In one form, a method includes applying to the defect a composition as described herein, preferably in the form of a moldable, yet hardenable, composition, such as a bone cement as described herein. The composition is applied by techniques known to the art and in an amount sufficient to correct the defect.

Reference will now be made to specific examples illustrating the compositions and methods above. It is to be understood that the examples are provided to illustrate preferred embodiments and that no limitation to the scope of the invention is intended thereby.

EXAMPLE 1

Fusion Cages Formed from Polyetheretherketone/Hydroxyapatite Compositions

A polyetheretherketone (PEEK)/hydroxyapatite (HA) composition may be utilized to form an intervertebral body fusion cage. A fusion cage may be fabricated by injection molding or by machining extruded bar stock of PEEK/HA nanocomposites. The bar stock may be produced using an extrusion process during which proportional quantities of PEEK resin pellets and HA nanoparticles are simultaneously fed into an extruder. A composition of 2 grams of PEEK per gram of HA may be used. As the PEEK polymer melts at approximately 340° C., HA nanoparticles are mixed and dispersed within the polymer prior to exiting the extruder. Extruded PEEK-HA nanocomposites can also be pelletized or chopped up into small pellets for the injection molding process.

EXAMPLE 2

Bone Cement Composition

A nanocomposite bone cement of polymethylmethacrylate (PMMA) and HA may be prepared by mixing a PMMA polymer powder and a methylmethacrylate monomer liquid by mixing methods known to the skilled artisan. The HA nanoparticles can be dispersed within the polymer powder, the monomer liquid or both in proportional quantities, such as 1 gram of HA per 5 grams of resulting bone cement. After mixing, the bone cement becomes a flowable homogeneous paste. The bone cement viscosity increases with time before setting up into a hard solid material. The PMMA-HA nanocomposite bone cement can be applied at any time during its uncured stage depending upon its final application, which may include vertebroplasty, arthroplasty, cranioplasty, or similar procedures.

The presence of HA may help reduce the heat release during exothermic polymerization that could adversely affect the host bone. Moreover, HA also works as a media contrast for visualization of cement flow under fluoroscopy in vertebroplasty.

EXAMPLE 3

Fusion Cages Formed From Poly(L-lactide-co-D,L-lactide)/Hydroxyapatite Compositions Fusion cages may be fabricated via injection molding or machining extruded bar stock of nanocomposites of poly(L-lactide-co-D,L-lactide) (PLDLA) (volume ratio of L-lactide to D,L-lactide of 70:30) and HA. The bar stock may be produced using an extrusion process during which proportional quantities of PLDLA resin granules and HA nanoparticles are simultaneously fed into an extruder. A 2:1 weight ratio of PLDLA:HA may be used. Prior to the extrusion process, PLDLA granules coated with a proportional quantity of HA nanoparticles can be obtained via blending a suspension of PLDLA and HA in ethanol and subsequent drying. As the PLDLA polymer melts approximately above 150° C., HA nanoparticles are mixed and dispersed within the polymer prior to exiting the extruder. Extruded PLDLA-HA nanocomposites can also be pelletized or chopped up into small pellets for the injection molding process.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. An orthopedic composition, comprising a homogeneous mixture of a biocompatible polymer, a bioactive particulate ceramic, said ceramic having an average particle size of not more than about 500 nm; and one or more growth factors selected from the group consisting of bone morphogenetic protein, LIM mineralization proteins, transforming growth factors, insulin-like growth factors, platelet-derived growth factors and fibroblast growth factors, wherein said growth factor is present in an amount of no more than about 5 weight percent.

2. The composition of claim 1, wherein at least about 30% of said particulate ceramic has an average particle size of not more than about 100 nm.

3. The composition of claim 1, wherein said ceramic has an average particle size of about 100 nm.

4. The composition of claim 1, wherein said ceramic has an average particle size of about 1 nm to about 500 nm.

5. The composition of claim 4, wherein said ceramic has an average particle size of about 1 nm to about 100 nm.

6. The composition of claim 5, wherein said ceramic has an average particle size of about 1 nm to about 50 nm.

7. The composition of claim 1, wherein said composition comprises about 1% to about 49% by volume of said ceramic and about 51% to about 99% by weight of said polymer.

8. The composition of claim 1, wherein said composition is comprised predominantly of said polymer.

9. The composition of claim 1, wherein said polymer is selected from a resorbable polymer and a non-resorbable polymer.

10. The composition of claim 1, wherein said polymer comprises polyetheretherketone, polyethylene, polymethylmethacrylate, poly(L-lactide), poly(D,L-lactide), poly(L-co-D,L-lactide), polyglycolide, poly(lactide-co-glycolide), poly (hydroxylbutyrate), poly(hydroxyvalerate), tyrosine-derived polycarbonate and combinations thereof.

11. The composition of claim 1, wherein said particulate ceramic is selected from bioactive glass and a calcium-containing ceramic.

12. The composition of claim 11, wherein said calcium-containing ceramic is a calcium phosphate-containing ceramic.

13. The composition of claim 12, wherein said calcium phosphate-containing ceramic is comprised of hydroxyapatite.

14. The composition of claim 1, wherein said homogeneous mixture is obtained by processing the ceramic, the polymer or a combination thereof, with carrier solvents.

15. A shaped, article formed from the composition of claim 1.

16. The article of claim 15, wherein said shaped article is a load bearing member.

17. The article of claim 16, wherein said member is an intervertebral disc implant.

18. The article of claim 16, wherein said article is shaped to form a structure selected from the group consisting of bone plates, bone screws and a load bearing intervertebral disc implant.

19. A bone cement formed from the composition of claim 1.

20. A composition according to claim 1 wherein said growth factor comprises one or more members selected from the group consisting of: bone morphogenetic protein, LIM mineralization proteins (LMPs), transforming growth factors, insulin-like growth factors, platelet-derived growth factors, and fibroblast growth factors.

* * * * *